US00PP28376P2

(12) United States Plant Patent
Horvath

(10) Patent No.: US PP28,376 P2
(45) Date of Patent: Sep. 12, 2017

(54) ***GEUM* PLANT NAMED 'COPPERTONE PUNCH'**

(50) Latin Name: ***Geum* hybrid**
Varietal Denomination: Coppertone Punch

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 14/999,396

(22) Filed: May 3, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Annette Para

(57) ABSTRACT

A new, distinct *Geum* plant as shown and described, characterized by overlapping orange petals of various length on semi-double deep orange flowers.

1 Drawing Sheet

Latin name: *Geum* hybrid.
Cultivar name: 'Coppertone Punch'.

BACKGROUND OF THE INVENTION

The present invention relates to a new and distinct hybrid of *Geum* plant named 'Coppertone Punch' characterized by overlapping orange petals of various length on semi-double deep orange flowers. The new *Geum* was discovered and developed as a seedling as part of an on going breeding and selecting program in Hebron, Ill. in 2010. The selection of the new plant was due to its' overlapping orange petals of various length on semi-double deep orange flowers. The initial asexual propagation of the new plant was by division and took place at a nursery in Hebron, Ill. since 2011. Continued asexual propagation by division since that time has shown that the unique features of this new *Geum* plant are stable and reproduced true to type in successive generations. No plants of the new *Geum* have been sold in this country, or anywhere in the world, prior to the filing of this application, nor has any disclosure of the new plant been made prior to the filing of this application with the exception of that which was disclosed within one year of filing of this application and was either derived directly or indirectly for the inventor.

SUMMARY OF THE INVENTION

In the following description, color references are made to The Royal Horticultural Society Colour Chart (2001). The new *Geum* plant named 'Coppertone Punch' is characterized by overlapping orange petals of various length on semi-double deep orange flowers of RHS N25 A.

The new *Geum* plant can be compared to 'Alabama Slammer' U.S. Plant Pat. No. 23,750, flower colors are orange RHS 44A blending into red RHS N34 while the new plant flower color is RHS N25 A.

The new plant can also be compared to *Geum* 'Totally Tangerine' U.S. Plant Pat. No. 22,041, which is a sterile hybrid with lighter orange single flowers of 32 A, that fades to 169 C. Plants of *Geum* 'Totally Tangerine' also grow to 130 cm tall while the new plant only grows 30-35 cm tall at maturity.

DESCRIPTION OF PHOTOGRAPHS

Figure 1:
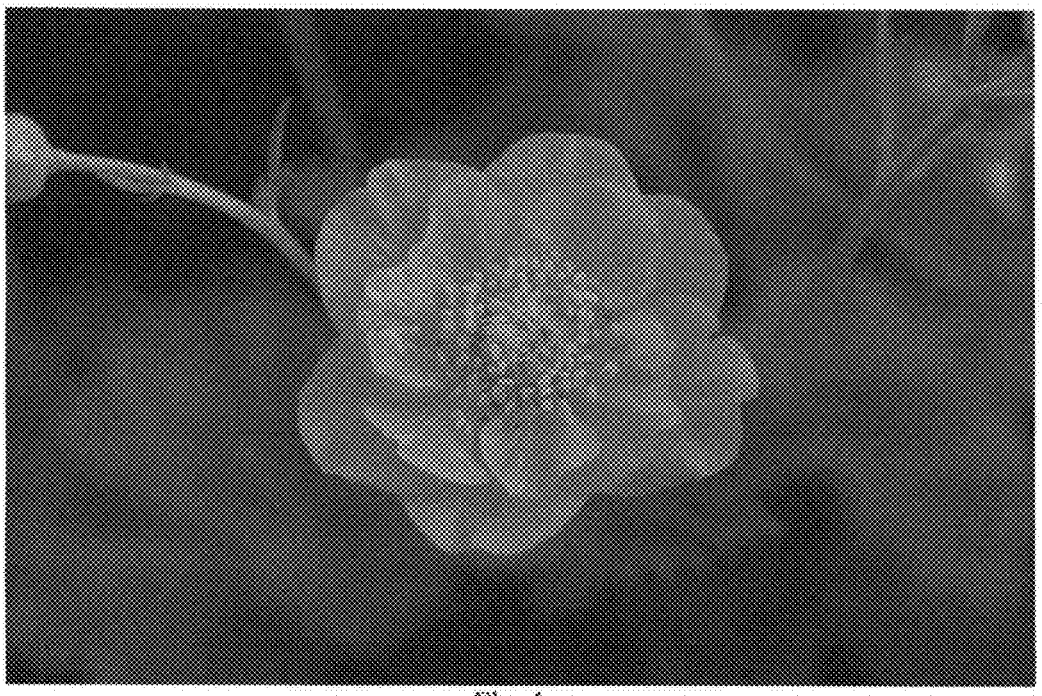
Figure 2:
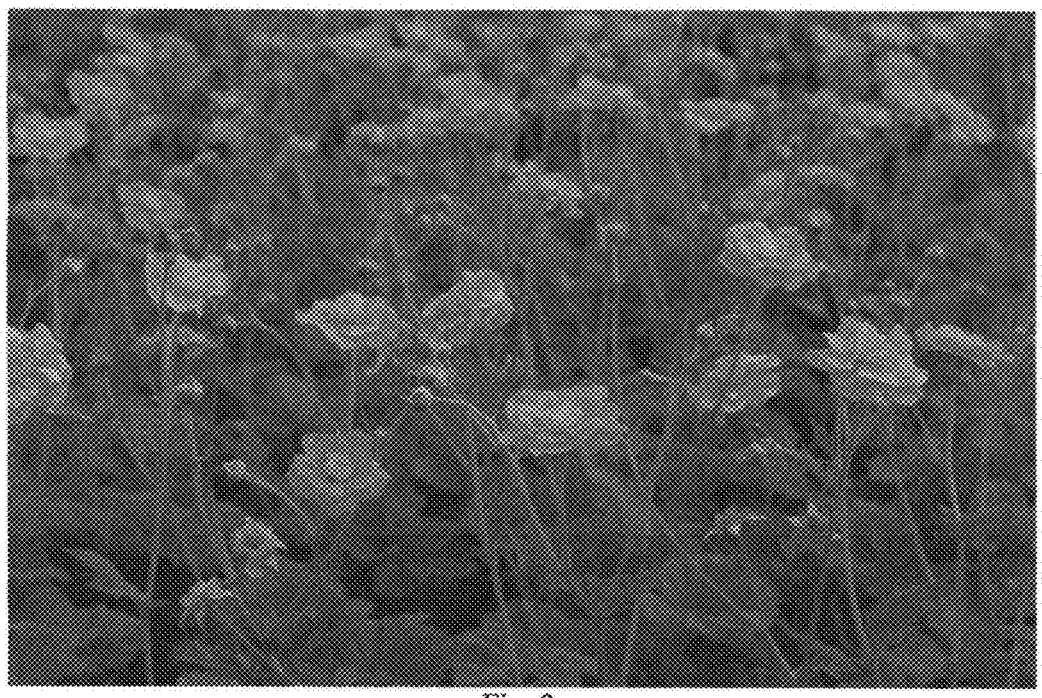

FIG. 1. Close up of the flower.
FIG. 2. Blooming plants in May.

DETAILED BOTANICAL DESCRIPTION

In the following description, color references are made to The Royal Horticultural Society Colour Chart (2001). Plants used for the description were grown in a trade one gallon container for one year at a nursery in Hebron, Ill. Measurements and numerical values represent averages of typical plants.

Botanical classification: *Geum* hybrid cultivar 'Coppertone Punch'.

Parentage: Unknown.

Propagation: Vegetative division.

Plant description: Overall habit of the new *Geum* is basal clumps, upright green flower stems topped by semi-double deep orange flowers of RHS N25 A.

*Plant type*.—Herbaceous perennial.

*Plant height*.—30-35 cm.

*Plant width*.—40 cm.

*Stem*.—Diameter: 2-3 mm.

*Stem or basal branches*.—Number of basal branches per plant: 14, length up to 35 cm, with the internode between basal foliage and first leaflet length being 7 cm and the second internode between the first leaflet and the second leaflet length being 5 cm and the third internode between the second and third leaflet length being 6 cm and the fourth internode between the third and fourth leaflet length being 2 cm.

*Stem coloration*.—146 D.

Foliage description:

*Type*.—Herbaceous.

*Arrangement*.—Basal alternate with typically two or three lateral leaflets per stem.

*Petiole*.—Up to 20 cm long, with a diameter of 3 mm, color 146 D.
*Terminal compound leaf length*.—Up to 4 cm.
*Terminal compound leaf width*.—3 cm.
*Terminal leaflet length*.—Typically 4 cm.
*Terminal leaflet width*.—Typically 3 cm.
*Terminal leaflet shape*.—Obovate with incised margins.
*Terminal and lateral leaf apex*.—Acute.
*Terminal and lateral leaf base*.—Cuneate.
*Terminal and lateral leaf margin*.—Incised.
*Texture*.—Terminal and lateral leaf, upper and lower surfaces: pubescent.
*Venation pattern*.—Terminal and lateral leaf, upper and lower surfaces: pinnate.
*Venation color*.—Terminal and lateral leaf, upper surface is color 146 A and lower surface color is close to 147 C.
*Lateral leaflet number*.—2 or 3 per stem.
*Lateral leaflet length*.—4 cm.
*Lateral leaflet width*.—Up to 2.5 cm.
*Lateral leaflet shape*.—Obovate.
*Adaxial leaf description*.—Color is close to 146 A.
*Abaxial leaf description*.—Color 148 B.

Flower description:

*Flower type*.—Corymb.
*Flower color*.—N25 A on top and N25 C on the bottum.
*Flower size*.—Diameter: 35 mm across, depth 10 mm.
*Flower number*.—4-5 per stem, 70 per plant.
*Number flowering stems*.—14.
*Bloom period and duration*.—Beginning the last week of April into the last week of May in Hebron, Ill.
*Flower longevity and duration on the plant*.—Approximately 3 weeks.
*Flower longevity and duration cut*.—Approximately one week.
*Individual flower duration*.—Approximately 1 to 2 weeks with petals eventually drying to a tan color.
*Scent*.—None.
*Petal count*.—10.
*Petal shape*.—Spatulate.
*Petal arrangement*.—Rotate, overlapping.
*Lower larger petal diameter or width*.—15 mm across and petal length — 14 mm long.
*Smaller top petal that lay on top of the diameter or width*.—9 mm across and petal length — 10 mm long.
*Petal apex*.—Retuse, base: attenuate, margin: entire.
*Petal texture*.—Upper and lower surfaces: smooth, glabrous.
*Petal color*.—Upper surface is color N25 A.
*Petal color*.—Lower surface color is close to N25 C.
*Overall corymb size*.—Diameter and height-11 cm across, 10 cm long.
*Flower buds*.—Diameter: 11 mm across, depth: 14 mm, shape: ovoid, surface: slightly pubescent and color 146 C.
*Sepal size*.—Length: up to 13 mm, diameter: 5 mm at base coming to a point.
*Sepal quantity*.—5.
*Sepal shape*.—Lanceolate, apex: acute, base: cuneate, margin: entire.
*Sepal texture*.—Upper and lower surfaces: Pubescent.
*Sepal color*.—Adaxial color is 146 C. Abaxial color 146 D.
*Peduncle color*.—Purple 146 D.
*Peduncle size*.—Length: 26 mm, diameter: 1-2 mm.
*Pedicel size*.—Length: 16 mm, diameter: 1-2 mm and color 146 D.
*Reproductive organs*.—Stamen — quantity over 100, length 3 cm.
*Anther*.—Quantity: over 100, length: 1 mm, diameter: close to 1 mm.
*Pollen*.—Typically present, color: 24 A.
*Stigma*.—Number over 50, width less than 1 mm, general color is orange.
*Style*.—Number: over 50, length: 6 mm, general color is 21 A.
*Pistil*.—Number over 50, length: 5 mm.
*Ovaries*.—Number: over 50 per bloom average, color: is green.
*Fruit*.—Number: over 50 per bloom average, color: is brown, tear shaped, length — 9-10 mm, width — 2 mm.
*Hardiness*.—USDA zone 4 to 9.

Disease resistance: Resistance to diseases common to *Geum* has not been observed on plants grown under nursery conditions.

I claim:

1. A new, distinct *Geum* plant as illustrated and described, characterized by overlapping orange petals of various length on semi-double deep orange flowers.

* * * * *